(12) United States Patent
Ibey et al.

(10) Patent No.: US 8,088,595 B2
(45) Date of Patent: Jan. 3, 2012

(54) METHOD FOR GLUCOSE MONITORING USING FLUORESCENCE QUENCHING

(75) Inventors: Bennett L. Ibey, College Station, TX (US); Vamsi K. Yadavalli, North Bethesda, MD (US); Rebecca M. Rounds, College Station, TX (US); Hope T. Beier, College Station, TX (US); Gerard L. Cote, College Station, TX (US); Michael V. Pishko, State College, PA (US)

(73) Assignee: The Texas A&M University System, College Station, TX (US)

( * ) Notice: Subject to any disclaimer, the term of this patent is extended or adjusted under 35 U.S.C. 154(b) by 55 days.

(21) Appl. No.: 12/660,884

(22) Filed: Mar. 5, 2010

(65) Prior Publication Data
US 2010/0222657 A1    Sep. 2, 2010

Related U.S. Application Data

(62) Division of application No. 11/529,280, filed on Sep. 28, 2006, now Pat. No. 7,704,704.

(60) Provisional application No. 60/721,447, filed on Sep. 28, 2005.

(51) Int. Cl.
C12Q 1/54        (2006.01)
(52) U.S. Cl. .......................................................... 435/14
(58) Field of Classification Search ...................... 435/14
See application file for complete search history.

(56) References Cited

U.S. PATENT DOCUMENTS

| | | | |
|---|---|---|---|
| 4,344,438 | A | 8/1982 | Schultz |
| 5,342,789 | A | 8/1994 | Chick et al. |
| 5,814,449 | A | 9/1998 | Schultz et al. |
| 6,256,522 | B1 | 7/2001 | Schultz |
| 6,454,710 | B1 | 9/2002 | Ballerstadt et al. |
| 6,485,703 | B1 | 11/2002 | Cotéet al. |
| 6,514,718 | B2 | 2/2003 | Heller et al. |
| 6,671,527 | B2 | 12/2003 | Petersson et al. |
| 6,885,882 | B2 | 4/2005 | Coté et al. |
| 7,704,704 | B2 * | 4/2010 | Ibey et al. .................... 435/14 |
| 2006/0247154 | A1 | 11/2006 | Palmieri et al. |
| 2007/0122829 | A1 | 5/2007 | Ballerstadt et al. |
| 2007/0148652 | A1 | 6/2007 | Norrid et al. |
| 2008/0188723 | A1 | 8/2008 | Kristensen et al. |

OTHER PUBLICATIONS

Ibey B. et al. Competitive Binding Assay for Glucose Based on Glycodendrimer-Fluorophore Conjugates. Analytical Chemistry 77(21)7039-7046, Nov. 1, 2005.*
*Biomedical Photonics Handbook* by Tuan Vo-Dinh, Crc Press, Jan. 24, 2003. (Coté, G.L., and McNichols, R.J., Glucose Diagnostics).
Rounds, R.M., Ibey, B.L., Beier, HT., Pishko, M.V, and Coté, G.L., "Microporated PEG Spheres for Fluorescent Analyte Detection", *J. of Fluorescence*, V17, N1, Jan. 2007.
Ibey, B.; Beier, H; Rounds, R.; Yadavalli, V.; Pishko, M.; Coté, G. "Competitive binding assay for glucose based on glycodendrimer-fluorophore conjugates" *Anal. Chem.* 2005, 77(21), 7039-7046.
Yadavalli, V.; Russell, R.; McShane, M.; Cote', G.; Pishko, M. "A Monte Carlo Simulation of Photon Propagation in Fluorescent Poly(ethylene glycol) Hydrogel Microsensors" *Sensors & Actuators B* 2005, 105, 365-377.
Yadavalli, V.; Pishko, M. "Biosensing in microfluidic channels using fluorescence polarization" *Anal. Chim. Acta.* 2004, 507(1), 123-128. 2004.
Yadavalli, V.; Koh, W.-G.; Lazur, G.; Pishko, M. "Microfabricated protein-containing poly(ethylene glycol) hydrogel arrays for biosensing" *Sensors & Actuators B: Chemical* 2004, 97(2-3), 290-297.
Coté, G.L., Lec, R.M., and Pishko, M.V., "Emerging Biomedical Sensing Technologies and Their Applications", IEEE Sensors Journal, V3, N3; pp. 251-66, Jun. 2003.
Coté, G.L., "Noninvasive and minimally invasive optical monitoring technologies", Journal of Nutrition, 131(5):1596S-604S, May 2001.
Russell, R.; Axel, A.; Shields, K.; Pishko, M. "Mass Transfer in Rapidly Photopolymerized Poly(ethylene glycol) Hydrogels Used for Chemical Sensing" *Polymer* 2001, 42, 4893-4901.
McShane, M.; Russell, R.; Pishko, M.; Cote, G. "Glucose Monitoring Using Implanted Fluorescent Microspheres" *IEEE Engineering in Medicine and Biology* 2000, 19(6), 36-45.
McShane, M.; Rastegar, S.; Pishko, M.; Coté, G. "Monte Carlo Modeling for Implantable Fluorescent Analyte Sensors" *IEEE Transactions in Biomedical Engineering* 2000, 47(5), 624-632.
McNichols, R.J., and Coté, G.L., "Optical Glucose Sensing in Biological Fluids: An Overview", *J. Biomedical Optics*, Cover Page, V5, N1, pp. 1-12, Jan. 2000.
Russell, R.; Simonian, A.; Wild, J.; Pishko, M. "Poly(ethylene glycol) Hydrogel Encapsulated Fluorophore-Enzyme Conjugates for Direct Detection of Organophosphorus Neurotoxins" *Anal. Chem.* 1999 71(21), 4909-4912.
Russell, R.; Gefrides, C.; McShane, M.; Coté, G.; Pishko, M. "A Fluorescence-Based Glucose Biosensor Based on Concanavalin a and Dextran Encapsulated in a Poly(ethylene glycol) Hydrogel" *Anal. Chem.* 1999, 71(15), 3126-3132.

(Continued)

*Primary Examiner* — Ralph Gitomer
(74) *Attorney, Agent, or Firm* — Baker Botts L. L. P.

(57) ABSTRACT

This disclosure relates to a method of measuring a glucose concentration metric or a glucose metric in a patient by contacting an implantable glucose-sensing device with a test sample, which may be in the patient, under conditions that permit a sugar-binding molecule and a functionalized polymer or nano-particle ligand present throughout the matrix of a hydrogel to interact in a glucose-dependent manner to produce an optical signal resulting from quenching of a first fluorophore linked to the ligand or sugar-binding molecule and having a fluorescent emission spectrum quenched upon binding or release of glucose. Next the first fluorophore may be excited with light of a certain wavelength. Then at least one wavelength of light in the glucose-dependent optical signal from the fluorophore may be detected with a detector to produce a detected light signal, which may be processed to produce a glucose metric, such as a glucose concentration metric.

24 Claims, 5 Drawing Sheets
(1 of 5 Drawing Sheet(s) Filed in Color)

OTHER PUBLICATIONS

Sirkar, K.; Pishko, M. "Amperometric Biosensors Based on Oxidoreductases Immobilized in Photopolymerized Poly(ethylene glycol) Redox Hydrogels" *Anal. Chem.* 1998, 70, 2888-2894.

Pishko, M. V.; Michael, A. C.; Heller, a. "Amperometric Glucose Microelectrodes Prepared through Immobilization of Glucose Oxidase in Redox Hydrogels" *Anal. Chem.* 1991, 63 (20), 2268.

Pishko, M. V.; Katakis, I.; Lindquist, S.-E.; Heller, A.; Degani, Y. "Electrical Communication Between Graphite Electrodes and Glucose Oxidase/Redox Polymer Complexes" *Mol. Cryst. Liq. Cryst.* 1990, 190, 221.

Pishko, M. V.; Katakis, I.; Lindquist, S.-E.; Ye, L.; Gregg, B. A.; Heller, A. "Direct Electrical Communication between Graphite Electrodes and Surface Adsorbed Glucose Oxidase/Redox Polymer Complexes" *Angewandte Chemie, International Ed.* 1990, 29 (1), 82.

Meadows, D., and Schultz, J.S., Fiber-optic biosensors based on fluorescence energy transfer, Talanta, V35/N2, pp. 145-150, 1988.

S. Mansouri, and J. S. Schultz, "A Miniature Optical Glucose Sensor Based on Affinity Binding," *Bio-Technology*, vol. 2, 1984, pp. 885-890.

J. S. Schultz, S. Mansouri, and I. J. Goldstein, "Affinity sensor: a new technique for developing implantable sensors for glucose and other metabolites," *Diabetes Care*, vol. 5, 1982, pp. 245-253.

J. S. Schultz, and G. Sims, "Affinity sensors for individual metabolites," *Biotechnology and bioengineering symposium*, vol. 9, 1979, pp. 65-71.

D. L. Meadows, and J. S. Schultz, "Design, Manufacture and Characterization of an Optical-Fiber Glucose Affinity Sensor-Based on an Homogeneous Fluorescence Energy-Transfer Assay System," *Analytica Chimica Acta*, vol. 280, 1993, pp. 21-30.

J. Lakowicz, and B. Maliwal, "Optical sensing of glucose using phase-modulation fluorimetry," *Anal. Chim. Acta* vol. 271, 1993, pp. 155-164.

L. Tolosa, L. Gryczynski, L. R. Eichhorn, J. D. Dattelbaum, F. N. Castellano, G. Rao, and J. R. Lakowicz, "Glucose sensor for low-cost lifetime-based sensing using a genetically engineered protein," *Anal Biochem* vol. 267, 1999, pp. 114-120.

R. Ballerstadt, C. Evans, A. Gowda, and R. McNichols, "In Vivo Performance Evaluation of a Transdermal Near-Infrared Fluorescence Resonance Energy Transfer Affinity Sensor for Continuous Glucose Monitoring," *Diabetes Technology & Therapeutics* vol. 8, 2006, pp. 296-311.

R. Ballerstadt, C. Evans, R. McNichols, and A. Gowda, "Concanavalin A for in vivo glucose sensing: A biotoxicity review," *Biosensors & Bioelectronics*, vol. 22, 2006, pp. 275-284.

R. Ballerstadt, A. Polak, A. Beuhler, and J. Frye, "In vitro long-term performance study of a near-infrared fluorescence affinity sensor for glucose monitoring," *Biosens Bioelectron*, vol. 19, 2004, pp. 905-914.

R. Ballerstadt, and J. S. Schultz, "A fluorescence affinity hollow fiber sensor for continuous transdermal glucose monitoring," *Anal Chem*, vol. 72, 2000, pp. 4185-4192.

L. Tolosa, H. Malak, G. Raob, and J. R. Lakowicz, "Optical assay for glucose based on the luminescence decay time of the long wavelength dye Cy5," *Sensors and Actuators, B: Chemical*, vol. B45, 1997, pp. 93-99.

L. Tolosa, H. Szmacinski, G. Rao, and J. R. Lakowicz, "Lifetime-Based Sensing of Glucose Using Energy Transfer with a Long Lifetime Donor," *Analytical Biochemistry*, vol. 250, 1997, pp. 102-108.

J. C. Pickup, F. Hussain, N. D. Evans, O. J. Rolinski, and D. J. Birch, "Fluorescence-based glucose sensors," *Biosens Bioelectron*, vol. 20, 2005, pp. 2555-2565.

J. C. Pickup, F. Hussain, N. D. Evans, and N. Sachedina, "In vivo glucose monitoring: the clinical reality and the promise," *Biosens Bioelectron*, vol. 20, 2005, pp. 1897-1902.

Beier, H.T., Ibey, B.L., Pishko, M., and Coté, G.L. "Use of glycosylated dendrimer macromolecules to fluorescently monitor glucose concentration", SPIE BIOS, Conf. 6445, San Jose, CA, Jan. 2007.

Rounds, R.M., Lee, S., Ibey, B.L., Pishko, M.V., and Coté, G.L., "Hydrogel microarrays for multi-analyte detection", SPIE BIOS, Conf. 6445, San Jose, CA, Jan. 2007.

Ibey, B.; Beier, H.; Rounds, R.; Pishko, M.; Cote, G. "Dendrimer based fluorescent glucose sensor for diabetic monitoring" *Proceedings—SPIE Optical Diagnostics and Sensing VI* 2006, 6904, 1-4.

Beier, H.; Ibey, B.; Rounds, R.; Pishko, M.; Cote, G. "Dendrimer optimization for a glucose-sensitive fluorescent assay" *Proceedings-SPIE Optical Diagnostics and Sensing VI* 2006, 6904, 65-68.

Rounds, R.M., Ibey, B.L., Beier, H.R., Pishko, M.V., and Coté, G.L., "Analysis of leeching and stability of microporated PEG spheres for fluorescent analyte detection", SPIE BIOS, Conf. 6094, San Jose, CA, Jan. 2006.

Ibey, B.; Yadavalli, V.; Thomas, H.; Rounds, R.; Pishko, M.; Cote, G. "Implantable fluorescence-based glucose sensor development" *Proceedings-SPIE* 2005, 5702, 1-6, *Optical Diagnostics and Sensing V*, Alexander V. Priezzhev, Gerard L. Cote Eds.

Ibey, B.; Meledeo, M.; Gant, V.; Yadavalli, V.; Pishko, M.; Cote, G. "In vivo monitoring of blood glucose using poly(ethylene glycol) microspheres" *Proceedings-SPIE* 2003, 4965, 1-6.

Ibey, B.L., Coté, G.L., Yadavalli, V., Gant, V.A., Newmyer, K., and Pishko, M.V., "Analysis of Longer Wavelength AlexaFluor Dyes for Use in a Minimally Invasive Glucose Sensor", IEEE EMBS Meeting, Cancun, Mexico, Sep. 17-21, 2003.

Meledeo, M.; Ibey, B.; O'Neal, P.; Pishko, M.; Coté, G. "Investigation of pH and temperature effects on FRET systems for glucose sensing" *Proceedings-SPIE* 2002, 4624, 55-65, *Optical Diagnostics and Sensing of Biological Fluids and Glucose and Cholesterol Monitoring II*, Alexander V. Priezzhev; Gerard L. Cote; Eds.

O'Neal, D. P.; McShane, M. J.; Pishko, M. V.; Cote, G. L. "Implantable biosensors: analysis of fluorescent light propagation through skin" *Proc. SPIE* 2001, 4263, 20-24, *Optical Diagnostics and Sensing of Biological Fluids and Glucose and Cholesterol Monitoring*, Alexander V. Priezzhev; Gerard L. Cote; Eds.

McShane, M.; O'Neal, D.; Russell, R.; Pishko, M.; Cote, G. "Progress toward implantable fluorescence-based sensors for monitoring glucose levels in interstitial fluid" *Proceedings-SPIE* 2000, 3923, 78-87.

McShane, M., Russell, R., Pishko, M., Rastegar, S., and Coté, G.L., "Optical system for implantable analyte sensors", Proceedings of the 1st Joint BMES/EMBS Conference (21st International Conference of the IEEE EMBS), pp. 804, Atlanta, GA, Oct. 13-16, 1999.

Russell, R.; Pishko, M.; Gefrides, C.; Cote, G. "A Fluorescent Glucose Assay using Poly-L-Lysine and Calcium Alginate Microencapsulated TRITC-Succinyl-Concanavalin A and FTIC-Dextran" *Proceedings of 20th Annual International Conference of the IEEE Engineering in Medicine and Biology Society* Oct. 29-Nov. 1, 1998, Hong Kong, p. 2858-2861.

McShane, M., Rastegar, S., and Coté, G.L., "Fluorescence-based implantable biosensors: Monte Carlo modeling for optical probe design", Proceedings of the 20th International Conference of the IEEE EMBS, Hong Kong, Oct. 29-Nov. 1, 1998.

Beier, H.T., Ibey, B.L., Pishko, M., and Coté, G.L. "Use of glycosylated dendrimer macromolecules to fluorescently monitor glucose concentration", SPIE BIOS, Conf. 6445, San Jose, CA, Jan. 2007.

Rounds, R.M., Lee, S., Ibey, B.L., Pishko, M.V., and Coté, G.L., "Hydrogel microarrays for multi-analyte detection", SPIE BIOS, Conf. 6445, San Jose, CA, Jan. 2007.

Ibey, B.; Beier, H.; Rounds, R.; Pishko, M.; Cote, G. "Dendrimer based fluorescent glucose sensor for diabetic monitoring" *Proceedings-SPIE Optical Diagnostics and Sensing VI* 2006, 6904, 1-4.

Rounds, R.M., Ibey, B.L., Beier, H.R., Pishko, M.V., and Coté, G.L., "Analysis of leeching and stability of microporated PEG spheres for fluorescent analyte detection", SPIE BIOS, Conf. 6094, San Jose, CA, Jan. 2006.

Ibey, B.; Yadavalli, V.; Thomas, H.; Rounds, R.; Pishko, M.; Cote, G. "Implantable fluorescence-based glucose sensor development" *Proceedings-SPIE* 2005, 5702, 1-6, Optical Diagnostics and Sensing V, Alexander V. Priezzhev, Gerard L. Cote, Eds.

Meledeo, M.; Ibey, B.; O'Neal, P.; Pishko, M.; Coté, G. "Investigation of pH and temperature effects on FRET systems for glucose sensing" *Proceedings-SPIE* 2002, 4624, 55-65, Optical Diagnostics and Sensing of Biological Fluids and Glucose and Cholesterol Monitoring II, Alexander V. Priezzhev; Gerard L. Cote; Eds.

O'Neal, D. P.; McShane, M. J.; Pishko, M. V.; Cote, G. L. "Implantable biosensors: analysis of fluorescent light propagation through skin" *Proc. SPIE* 2001, 4263, 20-24, Optical Diagnostics and Sensing of Biological Fluids and Glucose and Cholesterol Monitoring, Alexander V. Priezzhev; Gerard L. Cote; Eds.

O'Neal, D.; Russell, R.; Rastegar, S.; Pishko, M.; Cote, G. "Analysis of Fluorescence Light Propagation Through Skin for Biosensing" *Digest of Papers of the 2000 World Congress on Medical Physics and Biomedical Engineering and the Proceedings of the 22$^{nd}$ Annual International Conference of the IEEE Engineering in Medicine and Biology Society* 2000, Paper TU-B313-01.

Russell, R.; Cote, G.; Pishko, M. "Optical Glucose Sensors Based on Photopolymerized Poly(ethylene glycol) Hydrogels" *Digest of Papers of the 2000 World Congress on Medical Physics and Biomedical Engineering and the Proceedings of the 22$^{nd}$ Annual International Conference of the IEEE Engineering in Medicine and Biology Society* 2000, Paper TH-FXH-70.

McShane M., Russell, R., Pishko, M., Rastegar, S., and Coté, G.L., "Optical system for implantable analyte sensors", Proceedings of the 1$^{st}$ Joint BMES/EMBS Conference (21st International Conference of the IEEE EMBS), pp. 804, Atlanta, GA, Oct. 13-16, 1999.

McShane, M.J., Rastegar, S., and Coté, G.L., "Probe design for implantable fluorescence-based sensors", Proceedings of the SPIE International Symposium on Biomedical Optics, San Jose, CA.: Optical Diagnostics of Biological Fluids V3599; pp. 93-100, Jan. 23-29, 1999.

Cummins, B.M., Beier, H.T., Pishko, M.V., and Coté, G.L., "Optimization of a glycodendrimer-based glucose sensing assay", Poster PS 8A-93, Biomedical Engineering Society Annual Meeting, Pittsburgh, PA, Oct. 7-10, 2009.

Rounds, R.M., Ibey, B.L., Thomas, H.R., Pishko, M.V., and Coté, G.L., "Microporated PEG Spheres for Fluorescent Analyte Detection", Biomedical Engineering Society Annual Fall Meeting, Baltimore, M.D., Sep. 28-Oct. 1, 2005.

Thomas, H.R., Ibey, B.L., Rounds, R.M., Pishko, M.V., and Coté, G.L., "Development of a Chemical Assay for Detection of Glucose Concentration", Biomedical Engineering Society Annual Fall Meeting, Baltimore, M.D., Sep. 28-Oct. 1, 2005.

Ibey, B., Yadavalli, V., Thomas, H., Schengrund, C.L., Pishko, M., Coté, G.L., "Development of a implantable blood glucose monitor using a competitive binding fluorescent assay in poly(ethylene) glycol microspheres", Poster presentation at the 4$^{th}$ Annual Diabetes Technology Meeting, Oct. 28-30, 2004.

Coté, G.L. and Pishko, M.V., "Progress toward an implantable fluorescence glucose sensor", Pittsburgh Conference, Orlando, FL, Mar. 10-13, 2003.

Coté, G.L., and Pishko, M.P., "Subcutaneous fluorescence glucose sensing using a competitive binding assay", 224$^{th}$ National ACS Meeting, Boston, MA, Aug. 18, 2002.

Meledeo, A., O'Neal, D.P., Davis, J., Pishko, M., and Coté, G.L., "Development of a fluorescence-based polymer sensing system for glucose monitoring", Presentation at the 19th Annual Houston Conference on Biomedical Engineering Research, University of Houston, Houston TX: Feb. 8-9, 2001.

Coté, G.L., Russell, R., O'Neal, D.P., and Pishko, M.V., "Glucose sensing using dermally implantable fluorescent polymer spheres", Noninvasive Blood Analytes, for Advanced Technology Applications to Combat Casualty Care (ATACCC 2000) Meeting, Jointly sponsored by the US Army and Navy Combat Casualty Care Research Programs, Ft. Walton Beach, FL and Eglin AFB: Sep. 25-29, 2000.

Yadavalli, V.; Pishko, M. "Biosensing in microfluidic channels using fluorescence polarization" *Materials Research Society Proceedings* 2003, vol. 733, N7.11.

Mellott, M., Searcy, K. and Pishko, M. "Transport Properties of PEG Gels" *Proceedings of the 25$^{th}$ International Symposium on Controlled Release of Bioactive Materials* 1998, p. 900-901.

Coté, G.L., "Overview of noninvasive optical measurements with a focus on glucose sensing applications", Biomedical Engineering Society Annual Meeting, Cleveland Ohio, Oct. 10-13, 1998.

Coté, G.L., "Optical Approaches toward glucose measurement", Innovative Non- or Minimally Invasive Technologies for Health Monitoring and Nutritional Status in Mothers and Young Children, sponsored by the USDA Childrens Nutrition Research Center, Baylor College of Medicine, Houston, TX: Aug. 7-8, 2000.

Russell, R.J., Pishko, M.V., McShane, M.J., Coté, G.L., and Rastegar, S., "Monte Carlo simulations of photon propagation in poly(ethylene glycol) hydrogel-based fluorescent biosensors", American Chemical Society Spring National Meeting, San Francisco, CA, Mar. 26-30, 2000.

\* cited by examiner

METHOD FOR GLUCOSE MONITORING USING FLUORESCENCE QUENCHING

CROSS-REFERENCE TO RELATED APPLICATIONS

This application is a divisional of U.S. application Ser. No. 11/529,280 filed Sep. 28, 2006 entitled "Implantable System for Glucose Monitoring Using Fluorescence Quenching," now U.S. Pat. No. 7,704,704.

U.S. application Ser. No. 11/529,280 claims the benefit of U.S. Provisional Application No. 60/721,447 filed Sep. 28, 2005, the contents of which are incorporated herein, in their entirety, by reference.

GOVERNMENT RIGHTS

This invention was made with Government support via NSF Contract No. #BES9908439. The Government may have certain rights in this invention.

TECHNICAL FIELD

The present disclosure relates to systems, devices, and methods of sensing an analyte.

BACKGROUND

Commercial blood glucose sensors available for diabetics are chemical sensors based on the enzyme glucose oxidase which breaks down glucose, in the presence of oxygen, into hydrogen peroxide. The produced hydrogen peroxide reacts with either electrical or optical molecules, producing a change proportional to the amount of glucose within the blood volume. These commercial sensors may have an error of less than 15 mg/dL blood glucose concentration. They, however, have the disadvantage of requiring blood from the patient through either a forearm or finger prick, resulting in pain to the patient and also a potential risk of infection. It has been shown that the pain and embarrassment associated with repeated finger pricking results in low patient compliance.

SUMMARY

The present disclosure relates to systems, devices, and methods of sensing an analyte. According to some embodiments, an analyte may be selected from the group consisting of glucose, cholesterol, lactate, bilirubin, blood gases (e.g., pO2, pCO2, pH), urea, creatinine, phosphate, myoglobin, calcium, and hormones. Embodiments of this disclosure are elaborated with respect to glucose sensing for illustration purposes, not to exclude embodiments in which another analyte is selected. Sensing an analyte may include, for example, determining whether the analyte is present, determining changes in an analyte amount or concentration, and/or determining analyte amount or concentration.

According to some embodiments of the disclosure, a sensor (e.g., comprising chemically sensitive particles) may be intradermally implanted where it may sense glucose. A method of sensing glucose may include an affinity reaction coupled with a change in fluorescence that may be monitored with an external electro-optic device. For example, a method for sensing glucose may include contacting a ligand (e.g., dextran or dendrimer) and a sugar-binding lectin (e.g., Concanavalin A) with a test sample. A sensor of the disclosure may dramatically improve implantable glucose sensing performance and may have potential for use in both in vitro (i.e., cell culture monitoring) and in vivo (i.e., for diabetic glucose monitoring) applications.

Embodiments of the disclosure may provide a number of technical advantages. Embodiments of the disclosure may include all, some, or none of these advantages. For example, a disclosed sensor may have advantages over other sensor designs by improvement in key areas. First, the use of an optical-based sensing modality allows the sensor to be minimally invasive, meaning that after the implantation procedure the patient may not require any surgical procedures. The device may work passively by shining light through the skin without irritation allowing for continuous monitoring of blood glucose eliminating the need for constant blood withdrawal. Secondly, this sensing modality may have a much larger photonic response than other FRET based approaches resulting in much higher signal-to-noise. This may translate into better correlation to glucose and a sensor that is less prone to environment error. This large change in light intensity is preserved upon encapsulation in the final sensor. Previous modalities have suffered large reduction in signal upon encapsulation into the final biocompatible vehicle resulting in sensors which were not viable for long term use in human subjects. Lastly, the external portion of the sensor, a miniature fluorescent monitoring system, may be small and portable as compared to other systems which have yet to prove portability.

According to some embodiments of the disclosure, a method of sensing glucose may include (a) contacting an implantable glucose sensor with a test sample under conditions that permit the binding protein and ligand of the sensor to interact in a glucose dependent manner to produce a glucose-dependent signal, (b) detecting the glucose-dependent signal with a detector. A method may further include processing a glucose-dependent signal to produce a glucose metric.

Other technical advantages are readily apparent to one skilled in the art from the following figures, descriptions, and claims.

BRIEF DESCRIPTION OF THE DRAWINGS

The patent application file contains at least one drawing executed in color. Copies of this patent or patent application publication with color drawing(s) will be provided by the United States Patent and Trademark Office upon request and payment of the necessary fee.

Some specific example embodiments of the disclosure may be understood by referring, in part, to the following description and the accompanying drawings, wherein.

DETAILED DESCRIPTION

Figure 1:
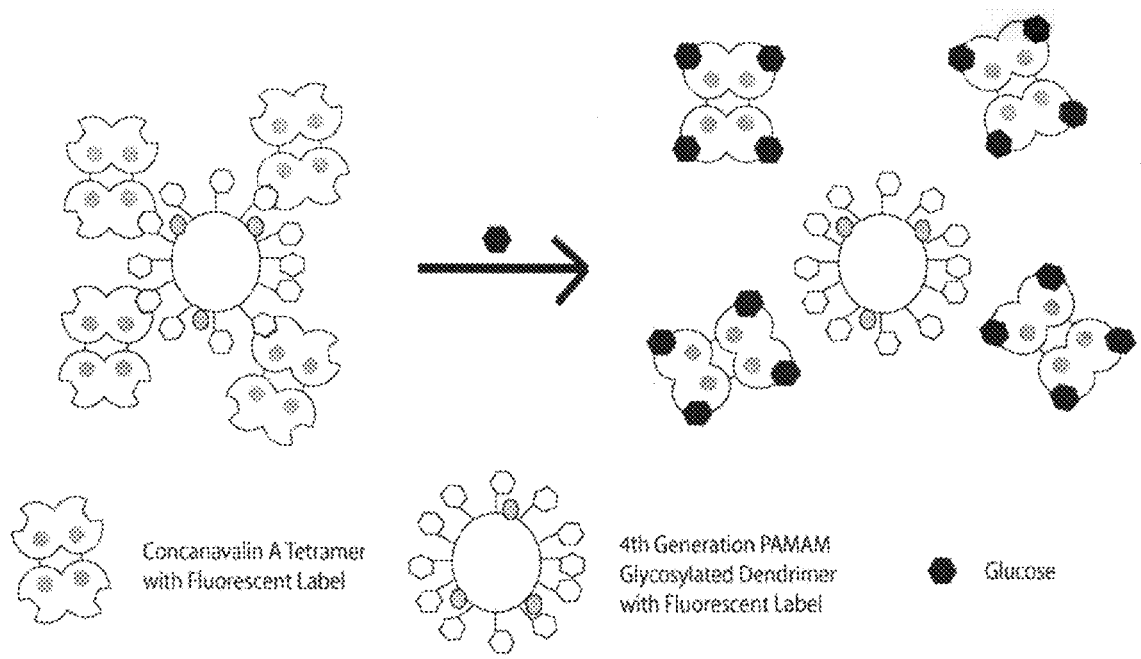
FIG. 1 is a schematic of a sensing chemistry according to an embodiment of the disclosure in which a fluorescently-labeled Concanavalin A tetramer binds to a fluorescently-labeled 4th generation PAMAM glycosylated dendrimer in a glucose-dependent manner.

In some embodiments, a device for sensing an analyte may include a ligand selected from the group consisting of dextran, functionalized polymers such as a glycosylated dendrimer, and functionalized nano-particles such as glycosyloxyethyl methacrylate (GEMA) immobilized on an active substrate such as a quantum dot, metal particle such as a gold or silver particle, or a gold nanoshell with silica core. An active particle may include a particle that participates in a fluorescent event, for example, by enhancing or quenching fluorescence. A device, in some embodiments may further include a sugar-binding lectin selected from the group consisting of Concanavalin A, glucose binding protein, glucose oxidase, and glucose apo-oxidase. A device may further include a first and second fluorophore, each of which is selected from the group consisting of fluoresceines, rhodamines, cyanines, and alexafluores, such as, but not limited to Alexa Fluor 594, Alexa Fluor 647. In some embodiments, the first fluorophore may be linked to the ligand and the second fluorophore may be linked to the sugar-binding lectin and the first fluorophore may be a fluorescence resonance energy transfer donor or a fluorescence resonance energy transfer acceptor. The second fluorophore, in some embodiments, may be a fluorescence resonance energy transfer donor or fluorescence resonance energy transfer acceptor. In some embodiments, a binding protein (e.g., Concanavalin A tetramer) may bind to a ligand (e.g., GEMA) in a glucose-dependent manner.

According to some embodiments, a fluorophore may be used as a baseline reference. For example, a sensor may be configured and arranged such that the absorption and/or emission spectra of this fluorophore is independent or substantially independent of an analyte metric (e.g., concentration). In some embodiments, a fluorophore may be a quenchable fluorophore. For example, a sensor may be configured and arranged such that the absorption and/or emission spectra of this fluorophore is dependent or substantially dependent on an analyte metric (e.g., concentration). In specific example embodiments, the emission spectra of a quenchable fluorophore may be quenched upon binding or release of an analyte. According to some embodiments, a system, device, or method may include both a reference fluorophore and a quenchable fluorophore. Comparing the absorption and/or emission spectra of the quenchable fluorophore with the absorption and/or emission spectra of the reference fluorophore may allow an analyte metric to be estimated, calculated and/or determined.

According to some embodiments, a binding protein may be free or immobilized on an active substrate or on an inactive substrate. In this context, an active substrate participates in the fluorescent event, for example, by enhancing or quenching the fluorescence (e.g., a quantum dot, metal particle such as a gold or silver particle, or a gold nanoshell with silica core) and an inactive substrate is one that does not participate in the fluorescent event but stabilizes the protein (e.g., a sepharose/polystyrene bead). A ligand, in some embodiments, may be immobilized on an active substrate.

A device of the disclosure may be comprised in a hydrogel, in some embodiments. A binding protein and/or a ligand may be dispersed in a hydrogel uniformly or non-uniformly as desired or required. A hydrogel may be porous or non-porous. Porosity may facilitate or may be adjusted to facilitate analyte access to the binding protein and/or ligand. Porosity may facilitate or may be adjusted to facilitate separation and/or binding of a binding protein and a ligand. A hydrogel, in some embodiments, may be partially or wholly enclosed within a membrane, e.g., a biocompatible membrane.

In some embodiments, a system for sensing glucose may include an implantable glucose-sensing device having (a) a hydrogel; (b) a ligand selected from the group consisting of dextran, functionalized polymers such as a glycosylated dendrimer, and functionalized nano-particles such as GEMA immobilized on an active substrate such as a quantum dot, metal particle such as a gold or silver particle, or a gold nanoshell with silica core; (c) a first fluorophore selected from the group consisting of fluoresceines, rhodamines, cyanines, and alexafluores, such as, but not limited to Alexa Fluor 594, Alexa Fluor 647, wherein the first fluorophore is linked to the ligand; (d) a sugar-binding lectin selected from the group consisting of Concanavalin A, glucose binding protein, glucose oxidase, and glucose apo-oxidase; and (e) a second fluorophore selected from the group consisting of fluoresceines, rhodamines, cyanines, and alexafluores, such as, but not limited to Alexa Fluor 594, Alexa Fluor 647, wherein the second fluorophore is linked to the sugar-binding lectin. A ligand and a sugar-binding lectin, in some embodiments, may be present throughout the matrix of the hydrogel or within pores in the hydrogel. A first fluorophore may be a fluorescence resonance energy transfer donor or fluorescence resonance energy transfer acceptor and the second fluorophore may be a fluorescence resonance energy transfer donor or fluorescence resonance energy transfer acceptor. A first fluorophore may be used as a baseline reference and a second fluorophore is quenched or a first fluorophore may be quenched and a second fluorophore may be used as a baseline reference.

A binding protein and a ligand, in some embodiments, may be configured and arranged to bind to each other in a glucose-dependent manner, for example, upon contact with a test sample. For example, a binding protein may be immobilized on an inactive substrate (e.g., a material that does not participate in the fluorescent event but stabilizes the protein). A non-limiting example of an inactive substrate is sepharose/polystyrene bead. A binding protein may be immobilized on an active substrate (e.g., a material that participates in the fluorescent event such as enhancing or quenching the fluorescence). Non-limiting examples of an active substrate include a quantum dot, a metal particle such as a gold or silver particle, and a gold nanoshell with silica core.

A system, according to some embodiments, may further include a light source, a detector, a processor, a power source, a display, memory, and/or an alarm. A light source, for example, may be configured and arranged to illuminate the implantable glucose sensing device with light of a wavelength sufficient to excite a first and/or a second fluorophore. Non-limiting examples of a light source include a laser diode, a light-emitting diode, light bulb (e.g., an incandescent light bulb), luciferase, and combinations thereof.

A detector may be (a) in optical communication with the implantable glucose sensing device and (b) configured and arranged to detect at least at least one wavelength of light from the implantable glucose sensing device and produce a detected light signal. Non-limiting examples of a detector include a photodiode having an interference filter, a prism or grating having a charge-coupled device array detection element, a photomultiplier tube, and combinations thereof.

A processor may be in communication with the detector and configured and arranged to receive and process at least one detected light signal to produce a glucose metric. A power source may be operably linked to at least the light source, the detector, and/or the processor. A non-limiting example of a power source is a battery. A display may be operably linked to the processor and configured and arranged to receive and display the glucose metric.

An alarm may be in communication with the processor and may be configured and arranged to alert when the glucose metric is above or below a preset threshold or within a preset range. An alarm alert may include an auditory and/or visual signal. In embodiments where a system further includes an insulin pump, an alert may include triggering the pump to alter (e.g., initiate, increase, decrease, discontinue) delivery of insulin to a subject.

A system according to some embodiments of the disclosure may include a housing, wherein the light source, the detector, the processor, and the power source are fully or at least partially enclosed within the housing. A housing may be configured and arranged to be worn by a subject. For example, a housing may be configured and arranged to place the light source and detector physical proximity of and optical communication with the implanted sensor. This may include contacting a subject's skin. A housing may be secured to a subject by available means including, without limitation, adhesives (e.g., tape), wraps (e.g., compression wrap), bands (e.g., watch band), and/or belts (e.g., waist belt).

Systems, devices, and methods, according to some embodiments of the disclosure may produce information that is representative of a glucose metric of a test sample. Non-limiting examples of a glucose metric include a glucose concentration, a change in glucose concentration, a rate of change of glucose concentration, an amount of glucose, a change in the amount of glucose, a rate of change of the amount of glucose, and combinations thereof.

A test sample may be a discrete volume or quantity of a composition. A test sample may include any composition in which glucose may be present, (e.g., control solution, a tear, interstitial fluid, plasma, whole blood). A test sample may be assayed in vitro, in situ, and/or in vivo. A subject may be any human or non-human animal. In embodiments where the subject is human, the subject may be the patient and/or the person seeking a glucose metric (e.g., a health care professional).

A method of sensing an analyte (e.g., glucose), according to some embodiments, may include implanting an implantable analyte sensor under the dermis of a subject. An implantable analyte sensor may be implanted directly through needle injection, air jet, or surgical procedure. A method of sensing glucose may include contacting an implantable glucose sensor with a test sample under conditions that permit the binding protein and ligand of the sensor to interact in a glucose dependent manner to produce a glucose-dependent signal (e.g., emission of or a change in the emission of at least one wavelength of light). Conditions that produce a glucose-dependent signal may include illuminating an implantable sensor (e.g., through the dermis) with at least one wavelength of light (e.g., quasi-monochromatic) that is sufficient to excite a first or second fluorophore. A glucose-dependent signal may include a change in the emission spectra of a first and/or second fluorophore. A change in the emission spectra of a first and/or second fluorophore may include a change in the fluence and/or wavelengths of light emitted. A glucose sensing method may further include detecting the glucose-dependent signal with a detector. A detector may include a photodiode with interference filters, a prism with a CCD array, or other wavelength separating optical modality.

In some embodiments of the disclosure, the binding affinity of the sugar-binding lectin for glucose is higher than the binding affinity for its binding affinity for the ligand (e.g., lower association constant). The lectin and the ligand may be selected and/or modified to modulate the degree to which the lectin reversibly binds glucose. For example, where consumption of lectin is not a concern (e.g., in a disposable sensor), lectin-glucose binding affinity may substantially higher (e.g., more than about 100-fold higher) than lectin-ligand binding affinity. On the other hand, where reversibility is desired or required, lectin-glucose binding affinity may higher than lectin-ligand binding affinity to the extent required to attain reversible binding. Reversible binding may occur where the lectin-glucose binding affinity is from about 1% to about 10-fold higher than the lectin-ligand binding affinity. Reversible binding may occur where the lectin-glucose binding affinity is more than about 5% higher than the lectin-ligand binding affinity. Reversible binding may occur where the lectin-glucose binding affinity is more than about 10% higher than the lectin-ligand binding affinity. Reversible binding may occur where the lectin-glucose binding affinity is more than about 15% higher than the lectin-ligand binding affinity. Reversible binding may occur where the lectin-glucose binding affinity is from about or over 10-fold higher than the lectin-ligand binding affinity.

According to some embodiments, a sensor and/or system of the disclosure may be configured and arranged to be minimally invasive. A sensor and/or system of the disclosure, in some embodiments may sense an analyte qualitatively, quantitatively, and/or semi-quantitatively. For example, a sensor and/or system may detect the presence or absence of an analyte. A sensor and/or system may measure the absolute and/or relative amount and/or concentration of an analyte. In some embodiments in which an analyte concentration is to be determined using an implantable sensor, the test sample volume may be measured, calculated, and/or estimated. For example, sample volume may be estimated based on the volume of an engorged sensor. Alternatively, a concentration may be determined on the basis of a calibration against a known standard. For example, glucose concentration may be monitored over a time period (e.g., 24 hours) using any available method to produce a glucose calibration curve. The signal produced by an implantable sensor over that same time period may be compared to the calibration curve to correlate the implantable sensor signal to glucose concentration. A sensor according to some embodiments of the disclosure may be configured and arranged to sense a wide or narrow range of glucose concentrations. For example, glucose-dependent signal produced by an implantable sensor may be linear up to about 600 mg/dL (e.g., from about 0 mg/dL to about 600 mg/dL).

Use of a minimally invasive technology for determination of blood glucose has been a pursuit of others. McShane et al. want to implant a polymeric sensor based upon monolayer self assembly that uses glucose oxidase similarly to the commercial blood withdrawal sensor. This sensor contains encapsulated glucose oxidase on a nanoparticle which, when implanted into the dermal layer of the skin, may react with native glucose and generate hydrogen peroxide. This reaction consumes oxygen and allows for an independent fluorescent ruthenium complex to change fluorescent emission due to the removal of quenching oxygen. This technology may work in vitro, but requires not only the consumption of oxygen within the tissue, but also consumption of glucose, which may result in ambiguous readings due to reduction in local glucose concentration around the sensor.

Sensing glucose with minimal invasiveness may include using a hydrogel contact lens comprising boronic acid. Boronic acid binds to glucose and changes its molecular characteristics (e.g., color) due to the binding. This approach may have the advantage of reversible binding so that glucose is not consumed as in the glucose oxidase based system. By using a modified system that contains two boronic acid tails attached to a polymer matrix, visible color changes may be seen in the contact lens upon exposure to different glucose concentrations. The glucose detected, using this sensor, may include tear glucose, the concentration of which may be an order of magnitude lower than concentration in blood.

One potential technology for near-continuous blood glucose detection is an implantable chemical assay based on a competitive binding reaction between the protein Concanavalin A (Con A), dextran, and glucose. For example, a sensor may be implanted superficially into the skin tissue and probe the interstitial fluid glucose concentration known to be comparable to that of the blood. Sensors may be based on a fluorescence resonance energy transfer (FRET) reaction between fluorescein isothiocynanate (FITC) labeled dextran and tetramethylrhodamine isothiocyanate (TRITC) labeled Concanavalin A (Con A). This heterogeneous FRET reaction may occur when one fluorophore is placed in close proximity (20-100) to a second fluorophore whose absorption spectrum heavily overlaps the emission spectrum of the first fluorophore. In the absence of glucose, the Con A tetramer binds to the dextran backbone, bringing the TRITC dye (Acceptor) within the Förster radius (e.g., 54 Å) of the FITC dye (Donor). Within the Förster radius, the FRET efficiency is above 50% and appears optically as an increase in the TRITC emission and a decrease in the FITC emission. Due to a higher affinity of Con A for glucose over dextran, glucose may bind to the Con A protein preferentially to displace the dextran chain which results in a change in fluorescent emission. Using the ratio between the two emission peaks, a quantitative measure of glucose concentration may be made.

A method and/or sensor, according to some embodiments of the disclosure, may use dendrimer molecules for sensing glucose in a biological environment. In some embodiments, a method and/or sensor may use pore forming material within a hydrogel. In some embodiments, a sensor may be configured and arranged as an external sensing device. Use of dendrimer may be important to the sensing modality, in some embodiments, because it may remove complications that limit other technology such as multivalent binding, small overall response, and repeatability as well as providing for increased dynamic range. One specific pore forming material is porogen, which forms pores within the hydrogel. In some embodiments, use of porogen may allow two components of the assay (e.g., ConA and dendrimer) to migrate away from each other, which is essential for the optical response and correct calibration of the instrument to glucose. In some embodiments, the external sensing device uses integrated electro-optics in a compact platform. This small platform allows for a watch type of device to be used to monitor the implant non-invasively and non-obtrusively in near real-time so that the patient may monitor themselves in the daytime and in the evening hours while sleeping. The device may also provide for an alarm to sound in order to warn or wake the patient in the event of extreme hypo- or hyper-glycemia.

In some embodiments, a sensor method and apparatus may measure interstitial fluid glucose concentration based on the interaction between a glycosylated dendrimer molecule and its interaction with a glucose binding ligand. In some embodiments, this ligand may include any suitable protein that exhibits a binding reaction with glucose and glycodendrimer molecules. A non-limiting example of a ligand is a ligand that is or includes Concanavalin A.

A sensor may be encapsulated by placing a sensing assay in a vehicle which readily dissolves in aqueous solution. In some embodiments, a vehicle may be insoluble or poorly soluble in poly(ethylene glycol) (PEG). Solubilizing a sensing assay may allow for the formation of small particles which may develop into pores by placing the sensor into an aqueous buffer. The use of other materials with similar porations may be included as well as the use of materials such as alginate, and silica bioglass. The final device may be an implantable sensor which may be placed under the dermis directly, for example, through needle injection, air jet, or surgical procedure.

This sensor may allow interstitial glucose to freely diffuse into the sensor cavity and cause the sensing element to change its fluorescent response dependent on the glucose level in the local environment. Therefore excitation (quasi-monochromatic) light may be projected through the skin by an external device and be absorbed by the fluorescent tags within the sensing element. This element may then alter the wavelength of this excitation light and back project the light out of the tissue and onto a detection element. This detection element may include a photodiode with interference filters, a prism with a CCD array, or other wavelength separating optical modality.

Implanted Sensing Element

Assay Chemistry:

The assay chemistry (FIG. 1) is based on the affinity binding of Concanavalin A to a glycosylated dendrimer and glucose found within the interstitial fluid. This reaction is optically probed by labeling both the Concanavalin A and glycosylated dendrimer with fluorescent molecules. The specific fluorophores used in the current prototype are Alexa Fluor 594 and Alexa Fluor 647 because they are reasonably efficient and of a proper wavelength to penetrate through the dermal tissue. These wavelengths are intended to be exemplary, not exclusive, and other FRET pairs may be possible. Other approaches may focus on the use of ConA and dextran, but fail to demonstrate stability over time and/or reliable reversibility. A dendrimer molecule, according to some embodiments of the disclosure, allows for nearly complete reversibility with limited hysteresis over time and has been shown to be stable at room temperature.

Figure 2:
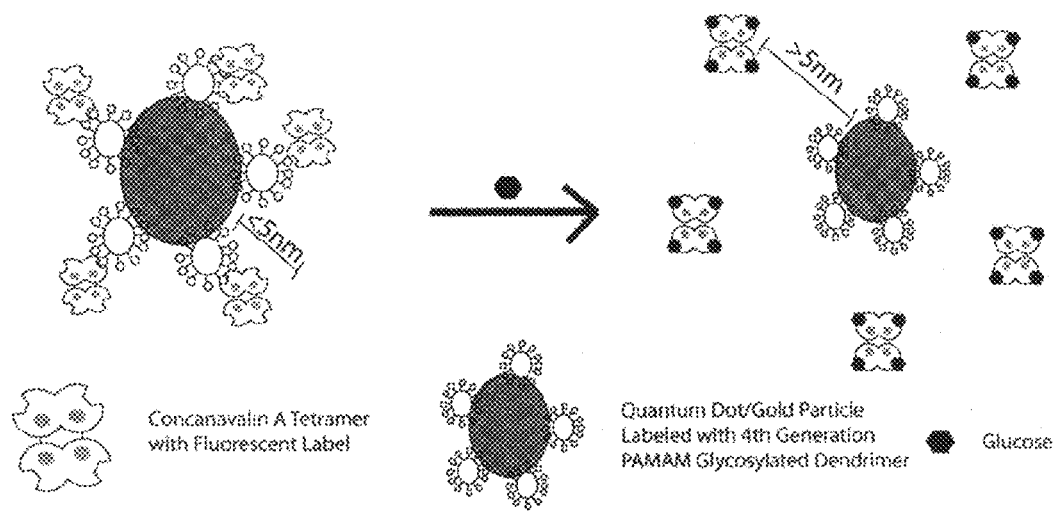
FIG. 2 is a schematic of a sensing chemistry according to an embodiment of the disclosure in which a fluorescently-labeled Concanavalin A tetramer binds to a fluorescently-labeled 4th generation PAMAM glycosylated dendrimer in a glucose-dependent manner wherein the dendrimer is immobilized on an active substrate (e.g., a quantum dot, metal particle)
Figure 3:
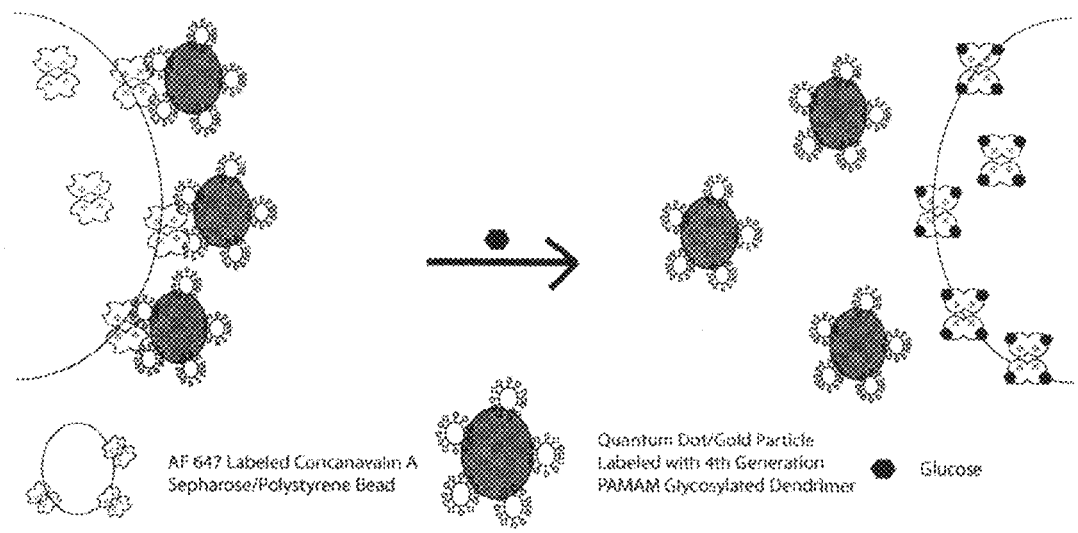
FIG. 3 is a schematic of a sensing chemistry according to an embodiment of the disclosure in which a fluorescently-labeled Concanavalin A tetramer binds to a fluorescently-labeled 4th generation PAMAM glycosylated dendrimer in a glucose-dependent manner wherein the Concanavalin A tetramer is immobilized on an inactive substrate (e.g., a sepharose/polystyrene bead) and the dendrimer is immobilized on an active substrate (e.g., a quantum dot, metal particle)
Figure 4:
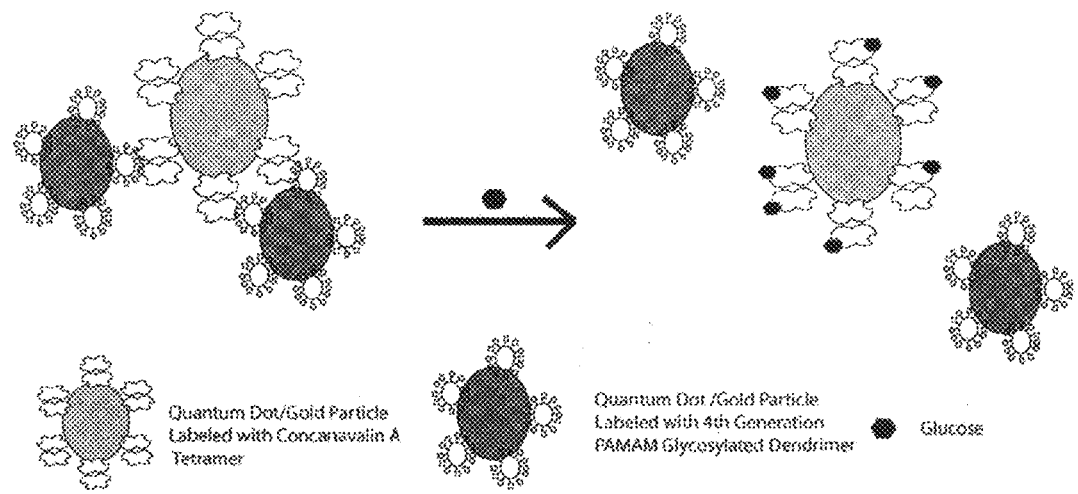
FIG. 4 is a schematic of a sensing chemistry according to an embodiment of the disclosure in which a Concanavalin A tetramer binds to a 4th generation PAMAM glycosylated dendrimer in a glucose-dependent manner wherein the Concanavalin A tetramer and the dendrimer are independently immobilized on active substrates (e.g., a quantum dot/gold particle)
Figure 5:
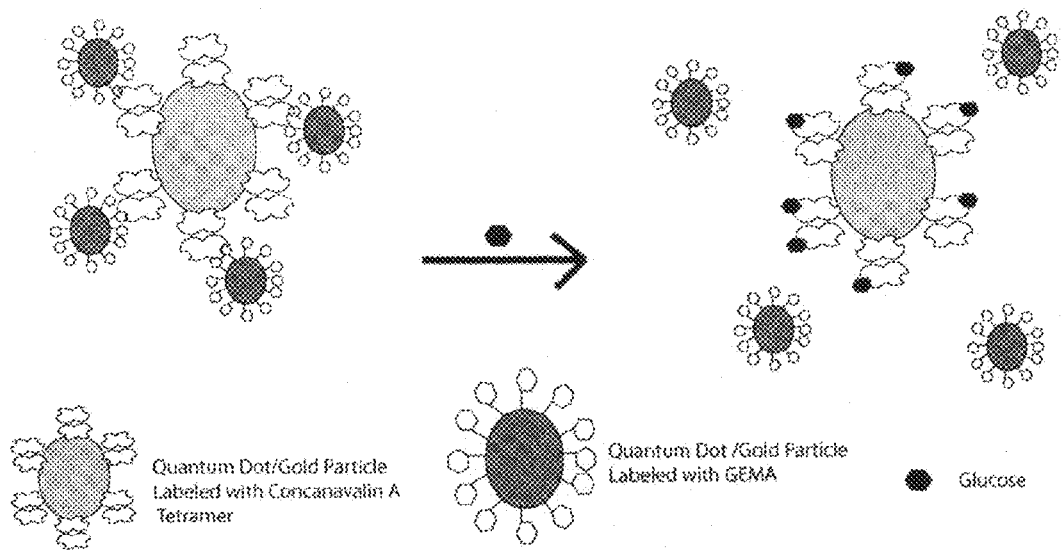
FIG. 5 is a schematic of a sensing chemistry according to an embodiment of the disclosure in which a Concanavalin A tetramer binds to glycosyloxyethyl methacrylate (GEMA) in a glucose-dependent manner wherein the Concanavalin A tetramer and the GEMA are each immobilized on an active substrate.

Sensing may also include introduction of an active immobilization substrate such as a metal nanoparticle (e.g., gold nanoshells, gold colloid, silver colloid) and/or quantum dot nanocrystals. These active substrates introduce the potential for large scale amplification of the fluorescent signal through an electromagnetic interaction with the emitting dyes. Example embodiments of the sensing approach are depicted in FIGS. 2, 3 and 4. The overall concept is the immobilization of the Con A protein onto a solid substrate to stabilize its binding confirmation thus enabling the lifetime of the sensor to increase dramatically. The devised assay may be contain a combination of gold particles and/or quantum dots precisely selected for maximum interaction upon binding to substantially increase the perceived optical change with glucose. In some embodiments, a quantum dot or gold particle may include a surface modification such as the addition of glycosyloxyethyl methacrylate (GEMA) molecule currently used to glycosylate a dendrimer surface in order to express saccharide terminal groups for binding to the Con A molecule (FIG. 5). The removal of the dendrimer surface group shortens the distance between the active substrates, which may increase the optical activity of the assay.

Figure 6:
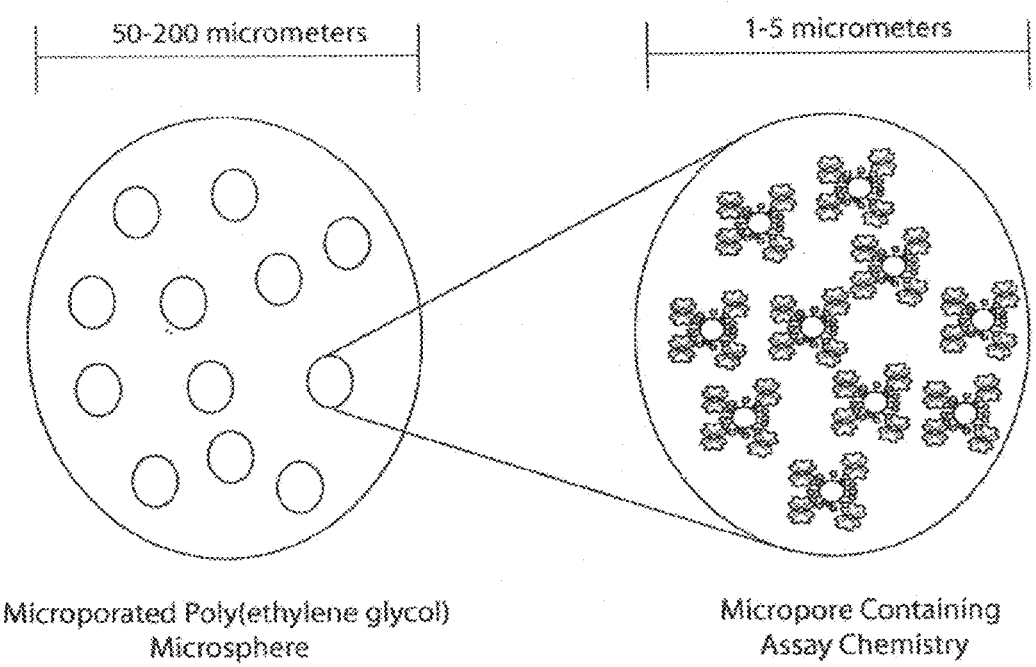
FIG. 6 is a schematic of the microporated polymer microspheres according to an embodiment of the disclosure.
Figure 7:
FIG. 7 is a combination fluorescent and brightfield image of a prototype microporated flourescent microspheres according to an embodiment of the disclosure.

Polymer Encapsulation:

The assay is encapsulated into a polymer hydrogel by using a novel microporation procedure which results in aqueous cavities being formed after the curation process (FIG. 6). The assay chemistry is mixed into a wet sample containing mannitol and dehydrated into a fine powder. This powder is then mixed into the polymer precursor solution and homogenized. This solution is then cured using an emulsion technique, which results in small spheres with solid mannitol contained within the material. Upon exposure to aqueous buffer, the mannitol (carrier material) dissolves, leaving an aqueous chamber containing the assay components (FIG. 7). Prior methods added the assay chemistry directly to the polymer precursor solution (10-50% water) along with a linker molecule which would bind the assay components (Con A protein and dextran) to the polymer subunits. This solution would be then cured to result in a dense polymer matrix surrounding the assay chemicals. This process did not yield a sensor sufficient to measure glucose through the dermal tissue due to limited mobility and leeching of the assay components.

Figure 8:
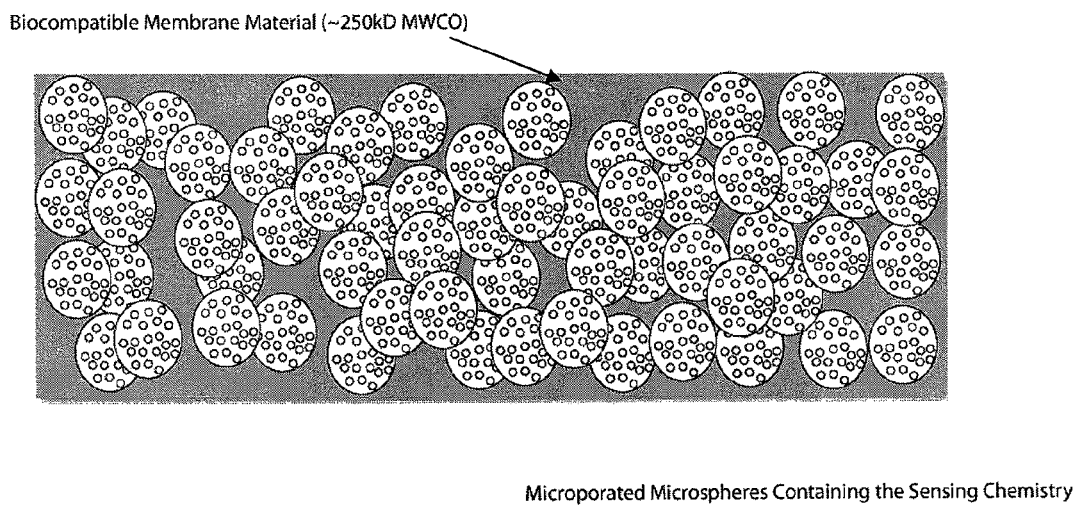
FIG. 8 is schematic of a biocompatible membrane to prevent microsphere migration according to an embodiment of the disclosure.

Membrane Net or Implantation Devices:

To implant the sensing modality into the dermal tissue various approaches have been investigated. The first approach, direct implantation into the skin, requires a large average sphere size, capable of being extracted, which results in a large response time. In order to reduce the response time of the sensor, multiple spheres are packaged into a permeable membrane which acts as a net holding the sensor spheres and allows for extraction from the dermal tissue (FIG. 8). The sphere package may be implanted using a plunger needle of adequate bore size to correctly implant the sensor with minimal dermal damage. Technologies similar to this have been used for dermal implantation of polymer based drug delivery systems. In this specific case, depth of implant may remain of importance due to the high scattering of light by the dermal tissue and the benefit of faster transport between blood and interstitial fluid by being close to the capillary bed. Therefore, our implantation device may be able to control for depth of implantation as well as physically implant the device.

External Sensing Element

Figure 9:
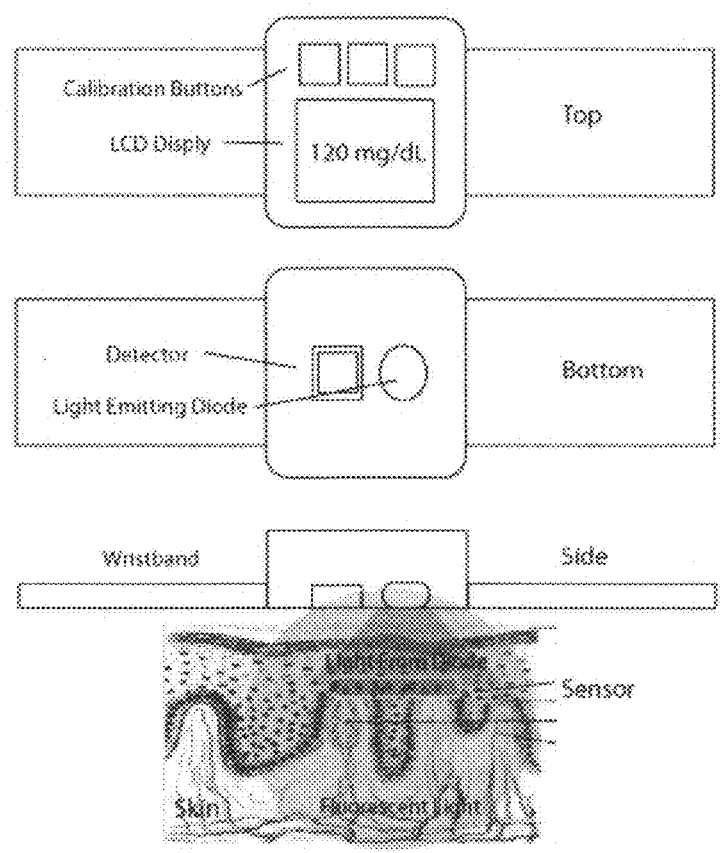
FIG. 9 is a schematic of an optical system and implanted sensor according to an embodiment of the disclosure.

Source Element:

The source element in the external sensing device may consist of a single lasing element such as a laser diode or a dispersive light source such as a LED centered at the proper wavelength (FIG. 9). The use of multiple wavelengths for multiple sensing elements within a single implant may be achieved by making a multi-channel multi-detector sensing structure, for example, with a minimum of two detectors to detect the two fluorescent peaks. A third detector may be included to account for other noise sources and baseline peaks. In some embodiments, a source may be powered by an on-board battery, for example, similarly to a watch. A system and/or device of the disclosure may, in some embodiments, be configured and arranged in a form resembling a wrist watch in size and shape. A system and/or device may sense glucose continuously, at regular intervals, at irregular intervals, and/or on demand. In addition, a system and/or device may include an alarm. An alarm may be set to alert a subject that analyte levels (a) within a range and/or (b) above or below a threshold have been detected. An alarm may be set to alert a subject that analyte trends have or have not occurred. An alarm may be set to alert a subject that one or more errors in analyte detection have occurred. A system and/or device may run unchecked for long periods of time (e.g., overnight) and/or may alert a subject of trends occurring during rest.

Detection Element:

The detection element present in the miniaturized external monitoring device may include a photodiode with an interference filter (e.g., long pass, band pass, notch), a prism with a CCD array detection element, or any other wavelength separating optical modality. In some embodiments, a detection system may be sensitive to small light intensities and include few or no moving parts. Also, a combination detector composed of multiple detectors with differing wavelength discrimination elements would be optimum to compensate for source and environment differences such as tissue (skin) hydration, changes in blood perfusion, and gross sensor movement. The signal acquired from the photonic instrumentation (current) would then be analyzed against the reference arm of the detection (source spectra) electronically to arrive at a value which is calibrated to glucose concentration and may be displayed on a LCD screen to the user. A system and/or device of the disclosure may be operably linked to a regulator and/or an insulin pump to administer insulin (or any other therapeutic preparation) when and to the extent indicated by detected glucose levels. A system and/or device may further include appropriate controls to ensure that neither too much nor too little of the therapeutic preparation is administered to a subject.

Holding Device:

The holding device may be a miniaturized circuit which contains the electronics for driving the source, detection elements, and processing and display elements with a small watch-like device. This technology may be further miniaturized into a completely implantable device capable of interacting directly with the sensing element and sending out information to a display/recording device outside of the tissue. The optical geometry of the instrument would be such to deliver and detect light with a small enough separation distance to ensure proper signal to noise and keep the device small. To ensure accuracy, this system may be made small enough to be redundant with multiple sources and detectors.

A system and/or device, according to some embodiments, may be configured to be minimally invasive, meaning that after the implantation procedure the patient will not require any surgical procedures. A system and/or device may work passively, for example, by shining light through the skin without irritation. This may allow continuous monitoring of blood glucose and/or eliminate the need for constant or repeated blood withdrawal. A system and/or device, according to some embodiments, may have a much larger photonic response than other FRET-based approaches resulting in much higher signal-to-noise. This may translate into better correlation to glucose and a sensor which is less prone to environment error. Changes in light intensity (e.g., large changes) may be preserved upon encapsulation in the final sensor. A system and/or device, according to some embodiments, may include a small, portable external fluorescent monitoring system. For example, a system and/or device may be configured and arranged to be worn by a subject on any portion of the body (e.g., finger, wrist, forearm, abdomen, ankle).

Implantable Sensor:

An implantable sensor design may include the use of dendrimer in an implantable sensing device for glucose. The methods of sensing disclosed may use the phenomenon of fluorescent emission for indirect sensing of glucose through molecule binding. However, other techniques such as Raman, absorption, scattering and fluorescent lifetime spectroscopy may also be used for monitoring the same chemical reaction. The sensing approaches and monitoring technique would be included in alternative embodiments of the same sensing assay. The use of poly(ethylene glycol) specifically in this assay is not limiting and poration of other acceptably biocompatible materials such as bioglass, alginate, etc. are included as alternative embodiments of sensor. Sensing components are not limited to Concanavalin A and dendrimer. Multiple protein and alternative binding molecules are present within current technology and may be implemented into this technology as with dendrimers that are modified with different terminal groups for the purpose of glucose sensing. Other methods of poration may also be used such as embedding of the sensing material into a micelle, red blood cell ghost, liposome, plant cell wall ghost, or other porogenation material. The sensor spheres themselves may be constructed using lithographic techniques, dropwise polymerization, or using an air misting technology. A device according to some embodiments of the disclosure may include larger sensor slabs. Appropriate compensation may be made for response time of these larger sensors.

External Sensing Element

Fluorescence intensity per se, may be hard to quantify because it may vary with the optical properties of the tissue. However, without being limited to any particular mechanism of action, the basic mechanism by which quenching occurs may be through a decrease in the fluorescence lifetime and lifetime measurements may potentially be less dependent on the tissue properties. Thus, according to an embodiment, an external sensing element may include a fluorescent lifetime detection system. The standard instrumentation for measuring fluorescence lifetime is more difficult than a simple intensity or spectral measurement and a much more costly endeavor. Thus, fluorescence lifetime may be measured, in some embodiments, by detecting a phase change between fluorescence emission and a modulated source. The phase approach uses standard optics and lasers to measure the phase difference between input and output signals but multiple scattering of light propagating in tissues may severely complicate any in vivo measurement of lifetime thus care must be taken with respect to calibration in order to yield quantifiable results. In this embodiment the device may incorporate both excitation and emission laser wavelengths. This dual wavelength approach, coupled with the diffusion model for optical propagation, may allow for the extraction of the fluorescent dye's lifetime independent of background scatter and absorption.

Current standard instrumentation for measuring fluorescence lifetime based on phase may be more difficult than a simple intensity or spectral measurement and may be a much more bulky instrument and more costly endeavor. Thus, in some embodiments, a fluorescence polarization (FP) technique may be used in which the degree of polarization of the fluorescence emission may be determined experimentally from the measurement of fluorescence intensities parallel and perpendicular with respect to the plane of linearly polarized excitation light and may be expressed in terms of polarization (P) or anisotropy (r) according to the equations below:

$$P = \frac{I_L - I_P}{I_L + I_P} \quad (1)$$

$$r = \frac{I_L - I_P}{I_L + 2I_P} \quad (2)$$

where $I_L$ is the fluorescence intensity parallel to the plane of the excitation light, $I_P$ is the fluorescence intensity perpendicular to the plane of the excitation light.

Both P and r are dimensionless quantities. Thus, this approach may be independent of dye concentration, intensity fluctuations of the light source or any inner filter effects. As FP results from the fundamental property of a molecule and since the reagents used are quite stable, it is relatively insensitive to instrumental changes such as drift and gain settings on the detection system, and is also less susceptible to environmental interferences such as pH changes when compared to assays based on fluorescence intensity measurements.

Without being limited to any particular mechanism of action, from a theoretical standpoint, the polarization of fluorescence emission of a fluorophore may be described by following equations:

$$\left(\frac{1}{P} - \frac{1}{3}\right) = \left(\frac{1}{P_0} - \frac{1}{3}\right)\left(1 + \frac{\tau}{\theta}\right) \quad (3)$$

$$\theta = \frac{\eta v}{kT} = \frac{\eta M}{RT}(v + h) \quad (4)$$

where $P$ is the polarization of the fluorescence observed in the absence of rotational diffusion, P is the polarization observed in the presence of rotational diffusion, $\tau$ is the fluorescence lifetime of the dye, $\theta$ is the rotational correlation time of the labeled macromolecule, k is the Boltzman constant, T is the absolute temperature (Kelvin), $\eta$ is the viscosity of the medium, V is the molecular volume of the labeled macromolecule, M is the molecular weight of the macromolecule, R is the ideal gas constant, v is the specific volume of the macromolecule and h is the hydration typically 0.2 g H20/g macromolecule. The fluorescence emission of a labeled macromolecule (such as an antibody or lectin conjugated with any fluorophore) when excited by a plane polarized light, is highly polarized if the macromolecule remains relatively stationary during the fluorophore's excitation lifetime. If the molecule rotates and vibrates during the excited lifetime of the fluorophore, its fluorescence emission may be depolarized, the extent of this depolarization being directly dependent on the rotational correlation time of the macromolecule (which in turn depends on the molecular weight of the labeled macromolecule conjugate), the solvent viscosity, lifetime of the fluorophore and temperature. Thus the fluorescence polarization of a labeled lectin or antibody may be expected to increase once it binds to its target protein or antigen or vice versa depending on molecular size due to the longer rotational correlation time of the larger complex as opposed to the smaller conjugate. According to equation 3, the polarization of the fluorescence is inversely proportional to the lifetime of the fluorophore, i.e., if the lifetime of the fluorophore decreases, the polarization of its fluorescence increases. This fact may be exploited in example embodiments of FRET-based fluorescence detection assays of the disclosure. When monitoring the fluorescence of the donor fluorophore in the FRET pair, in the event when there is an appreciable transfer of energy from the donor to the acceptor, the lifetime of the donor ($\tau$) may decrease as an additional pathway for the evacuation of the energy at the excited level from the donor to the acceptor is created. This may lead to an increase in the polarization (P) of the fluorescence emission of the donor (see Eq. 3) in the case where FRET is occurring as opposed to when there is no FRET occurring. In some embodiments, a key to the success of a fluorescence-based assay may be the development and/or appropriation of a dye with a suitable lifetime that may capture the changes in molecular rotational times that occur during the interactions. Traditional fluorophores such as fluorescein or rhodamine with lifetimes around four nanoseconds may be used in fluorescence polarization assays in which the molecular weight of the labeled entity is less than a few thousand Daltons. However, longer lifetime dyes such as the ruthenium based metal-ligand complexes (MLC) manufactured by Fluka Corporation have lifetimes ranging from 400 to 800 nanoseconds, thus allowing the analysis of biological systems with molecular weights up to 10 million Daltons and correlation times up to 8 µsec. In some embodiments, fluorescence polarization of the donor dye may be affected by both its rotational motion (depending on the molecular weight of dye/macromolecule complex) as well as its lifetime (depending on the extent of FRET occurring) and thus may provide an increase in the sensitivity of the assay.

Thus, ruthenium MLC dye may be used at longer wavelengths in a FRET Polarization assay to provide a sensitive bio-analyte detection technique. In some embodiments, an inexpensive system may include a laser diode (or alternatively a xenon arc lamp and wavelength filter), a polarizer, a regular off the shelf miniature spectrometer (that may eventually be replaced with two filters) and two polarizers (analyzers) oriented perpendicular coupled to two detectors. This does increase the complexity slightly since polarization optics are added but the cost of such a system should remain low and be able to be incorporated ultimately in a small "watch sized" device.

According to some embodiments, a system, device, and/or method may extend into implementing other sensing assays into polymer spheres and using these sensing technologies in cell culture monitoring. A system, device, and/or method may include optimization of a sensor including miniaturization and implantation into a human and/or a non-human animal subject.

Although embodiments of the disclosure and their advantages are described in detail, a person skilled in the art may make various alterations, additions, and omissions without departing from the spirit and scope of the present disclosure. As will be understood by those skilled in the art, other equivalent or alternative systems, devices, and/or methods for sensing glucose according to embodiments of the present disclosure can be envisioned without departing from the essential characteristics thereof. For example, systems and devices of the disclosure may be manufactured in any desired size including, without limitation, a handheld or a tabletop configuration. Systems, devices, and methods of the disclosure may be adapted for use in disposable strips. For example, a ligand and a lectin may be printed on a substrate configured to contain a small volume of test sample (e.g., about or less than 1 µL). The substrate may be integrated with or separate from other elements (e.g., light source, detector, processor, display). Systems and devices of the disclosure may be operated sporadically, intermittently, and/or continuously. Also, light sources or light emission optics other than lasers including and not limited to incandescent light and narrowband light sources appropriately tuned to the desired wavelengths and associated light detection optics may be included in devices of the disclosure. A light source and/or detector may be placed near the tissue location or may be positioned within a remote unit. Light may be delivered to and/or received from an implantable sensor and/or tissue location via optical fibers. Disclosures of hypotheses, theories, or mechanisms of action represent possible explanations for observed features, behaviors and/or performance, but should not be deemed to limit or control all embodiments of the disclosure. These equivalents and alternatives along with obvious changes and modifications are intended to be included within the scope of the present disclosure. Accordingly, the foregoing disclosure is intended to be illustrative, but not limiting, of the scope of the disclosure as illustrated by the following claims.

What is claimed is:

1. A method of measuring a glucose concentration metric, said method comprising:

contacting an implantable glucose-sensing device with a test sample under conditions that permit a sugar-binding molecule comprising Concanavalin A, other sugar-binding lectins, glucose binding protein, glucose oxidase, or glucose apo-oxidase, the sugar binding molecule present throughout a matrix of a hydrogel in the glucose-sensing device and a functionalized polymer or functionalized nano-particle ligand present throughout the matrix of the hydrogel in the glucose-sensing device to interact in a glucose-concentration dependent manner to produce a glucose-concentration-dependent optical signal resulting from quenching of a first fluorophore comprising a fluorescein, a rhodamine, a cyanine, or fluorescent dye, the first fluorophore linked to the ligand or sugar-binding molecule and having a fluorescent emission spectrum quenchable upon binding or release of glucose by the sugar-binding molecule;

exciting the first fluorophore with light of a wavelength sufficient to excite the fluorophore;

detecting at least one wavelength of light in the glucose-concentration-dependent optical signal from the fluorophore with a detector to produce a detected light signal; and processing the detected light signal to produce a glucose concentration metric.

2. The method according to claim 1, further comprising displaying the glucose concentration metric on a display.

3. The method according to claim 1, wherein the glucose concentration metric is selected from the group consisting of a glucose concentration, a change in glucose concentration, a rate of change of glucose concentration, an amount of glucose, and combinations thereof.

4. The method according to claim 1, further comprising triggering an alarm when the glucose concentration metric is below a preset threshold.

5. The method according to claim 1, further comprising triggering an alarm when the glucose concentration metric is above a preset threshold.

6. The method according to claim 1, further comprising triggering an alarm when the glucose concentration metric is within a preset range.

7. The method according to claim 1, further comprising detecting at least one wavelength of light in an optical signal a second fluorophore in the glucose-sensing device, the second fluorophore comprising a fluorescein, a rhodamine, a cyanine, or fluorescent dye linked to the sugar-binding molecule or ligand to which the first fluorophore is not linked.

8. The method according to claim 7, further comprising:
processing the detected light signal from the second fluorophore; and
altering the glucose concentration metric based on the detected light signal from the second fluorophore.

9. The method according to claim 1, wherein the functionalized polymer or functionalized nano-particle ligand comprises a glycosylated dendrimer and contacting the implantable glucose-sensing device with a test sample under conditions that permit the sugar-binding molecule and the functionalized polymer or functionalized nano-particle ligand to interact in a glucose-concentration-dependent manner to produce a glucose-concentration-dependent optical signal comprises contacting under conditions that permit the sugar-binding molecule and the glycosylated dendrimer to interact.

10. The method according to claim 1, wherein the sugar binding molecule present and the functionalized polymer or functionalized nano-particle ligand are present throughout in pores of the hydrogel and contacting comprises contacting under conditions that permit the sugar-binding molecule and the functionalized polymer or functionalized nano-particle ligand to interact in the pores.

11. A method of measuring glucose concentration in a patient, said method comprising:
implanting an implantable glucose-concentration-sensing device in a patient;
contacting an implantable glucose-concentration-sensing device with a test sample under conditions that permit a sugar-binding molecule comprising Concanavalin A, other sugar-binding lectins, glucose binding protein, glucose oxidase, or glucose apo-oxidase, the sugar binding molecule present throughout a matrix of a hydrogel in the glucose-concentration-sensing device and a functionalized polymer or functionalized nano-particle ligand present throughout the matrix of the hydrogel in the glucose-sensing device to interact in a glucose-concentration-dependent manner to produce a glucose-concentration-dependent optical signal resulting from quenching of a first fluorophore comprising a fluorescein, a rhodamine, a cyanine, or fluorescent dye, the first fluorophore linked to the ligand or sugar-binding molecule and having a fluorescent emission spectrum quenchable upon binding or release of glucose by the sugar-binding molecule;
exciting the first fluorophore with light of a wavelength sufficient to excite the fluorophore;
detecting at least one wavelength of light in the glucose-dependent optical signal from the fluorophore with a detector to produce a detected light signal; and
processing the detected light signal to produce a glucose concentration metric reflective of the glucose concentration in the patient.

12. The method according to claim 11, further comprising displaying the glucose concentration metric on a display.

13. The method according to claim 11, wherein the glucose concentration metric is selected from the group consisting of a glucose concentration, a change in glucose concentration, a rate of change of glucose concentration, and combinations thereof.

14. The method according to claim 11, further comprising triggering an alarm when the glucose concentration metric is below a preset threshold.

15. The method according to claim 11, further comprising triggering an alarm when the glucose concentration metric is above a preset threshold.

16. The method according to claim 11, further comprising triggering an alarm when the glucose concentration metric is within a preset range.

17. The method according to claim 11, further comprising detecting at least one wavelength of light in an optical signal a second fluorophore in the glucose-sensing device, the second fluorophore comprising a fluorescein, a rhodamine, a cyanine, or fluorescent dye linked to the sugar-binding molecule or ligand to which the first fluorophore is not linked.

18. The method according to claim 17, further comprising:
processing the detected light signal from the second fluorophore; and
altering the glucose concentration metric based on the detected light signal from the second fluorophore.

19. The method according to claim 11, further comprising placing a housing containing at least the glucose-concentration-sensing device on the patient.

20. The method according to claim 19, wherein placing the housing on the patient comprises placing the housing on skin of the patient.

21. The method according to claim 11, wherein implanting comprises implanting the glucose-concentration-sensing device under the dermis of the patient.

22. The method according to claim 11, wherein implanting comprises needle injection, air jet injection, or a surgical procedure.

23. The method according to claim 11, wherein the functionalized polymer or functionalized nano-particle ligand comprises a glycosylated dendrimer and contacting the implantable glucose-concentration-sensing device with a test sample under conditions that permit the sugar-binding molecule and the functionalized polymer or functionalized nano-particle ligand to interact in a glucose-concentration-dependent manner to produce a glucose-concentration-dependent optical signal comprises contacting under conditions that permit the sugar-binding molecule and the glycosylated dendrimer to interact.

24. The method according to claim 11, wherein the sugar binding molecule present and the functionalized polymer or functionalized nano-particle ligand are present throughout in pores of the hydrogel and contacting comprises contacting under conditions that permit the sugar-binding molecule and the functionalized polymer or functionalized nano-particle ligand to interact in the pores.

* * * * *

UNITED STATES PATENT AND TRADEMARK OFFICE
CERTIFICATE OF CORRECTION

PATENT NO.        : 8,088,595 B2
APPLICATION NO.   : 12/660884
DATED             : January 3, 2012
INVENTOR(S)       : Ibey et al.

Page 1 of 1

It is certified that error appears in the above-identified patent and that said Letters Patent is hereby corrected as shown below:

Please amend the patent as follows:

Column 1, Lines 19-21, GOVERNMENT RIGHTS

This invention was made with Government support ~~via NSF~~ under ~~Contract No.# BES9908439~~ BES-9908439 awarded by National Science Foundation (NSF). The Government ~~may have~~ has certain rights [[to]] in ~~this~~ the invention.

Signed and Sealed this
Tenth Day of April, 2012

David J. Kappos
*Director of the United States Patent and Trademark Office*